United States Patent
Skuballa et al.

Patent Number: 4,487,953
Date of Patent: Dec. 11, 1984

[54] 9-BROMOPROSTAGLANDINS, THEIR PREPARATION, AND THEIR USE AS MEDICAMENTS

[75] Inventors: Werner Skuballa; Bernd Raduechel; Norbert Schwarz; Helmut Vorbrueggen; Walter Elger, all of Berlin, Fed. Rep. of Germany

[73] Assignee: Schering Aktiengesellschaft, Berlin and Bergkamen, Fed. Rep. of Germany

[21] Appl. No.: 446,888

[22] Filed: Dec. 6, 1982

[30] Foreign Application Priority Data

Dec. 4, 1981 [DE] Fed. Rep. of Germany ....... 3148743

[51] Int. Cl.³ ............................................ C07C 177/00
[52] U.S. Cl. ........................................ 560/55; 560/17; 560/121; 562/426; 562/465; 562/504; 564/175; 564/189; 564/162; 564/89; 564/92; 549/429; 549/504; 549/74; 549/79; 556/482; 568/649; 568/807; 568/669; 568/608; 548/201; 548/215; 544/242; 424/308; 424/317; 424/320; 424/305
[58] Field of Search .................. 560/121, 55; 568/649, 568/807, 669, 608; 564/80, 89, 92, 102, 162; 424/308, 305, 317; 562/465, 503

[56] References Cited
FOREIGN PATENT DOCUMENTS 2950027 11/1981 Fed. Rep. of Germany ...... 560/121

OTHER PUBLICATIONS

Arroniz et al., Synthesis of Ring Halogenated Prostaglandins (1), Prostaglandins 16, 47, (1978).

Primary Examiner—Paul J. Killos
Attorney, Agent, or Firm—Millen & White

[57] ABSTRACT

Compounds of Formula (I)

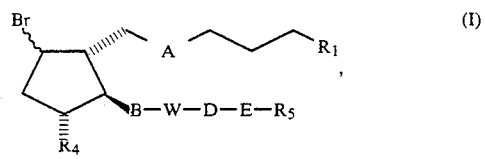

wherein
the 9-bromine atom can be in the α- or β-position,
$R_1$ is $CH_2OH$ or $C(O)OR_2$, wherein $R_2$ is hydrogen, alkyl, cycloalkyl, aryl, or a heterocyclic residue; or $R_1$ is $C(O)NHR_3$ wherein $R_3$ is an acid residue or $R_2$; and
A is $-CH_2-CH_2-$ or cis $-CH=CH-$;
B is $-CH_2-CH_2-$, trans $-CH=CH-$, or $-C\equiv C-$;
W is a free or functionally modified hydroxymethylene group or a free or functionally modified

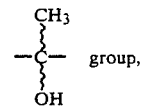 group, wherein the OH-group can be in the α- or β-position;
D and E together are a direct bond; or
D is straight-chain, branched, or cyclic alkylene of 1–10 carbon atoms, optionally substituted by fluorine atoms; and
E is oxygen, sulfur, a direct bond $-C\equiv C-$, or $-CR_6=CR_7-$, wherein $R_6$ and $R_7$ are different from each other and each is hydrogen, chlorine, or $C_1-C_4$-alkyl;
$R_4$ is a free or functionally modified hydroxy group;
$R_5$ is hydrogen, alkyl, halo-substituted alkyl, cycloalkyl, optionally substituted aryl, or a heterocyclic group; and, when $R_2$ is hydrogen, the salts thereof with physiologically compatible bases, are pharmacologically active compounds, e.g., as abortifacients.

37 Claims, No Drawings

9-BROMOPROSTAGLANDINS, THEIR PREPARATION, AND THEIR USE AS MEDICAMENTS

BACKGROUND OF THE INVENTION

The present invention relates to novel 9-bromoprostaglandin derivatives, a process for their preparation, and their use as medicaments.

It is known from the very voluminous state of the art of prostaglandins and their analogs that this class of compounds, due to their biological and pharmacological properties, are suitable for the treatment of mammals, including man. Their use as medicines, however, frequently presents difficulties. Most of the natural prostaglandins have a period of efficacy too brief for therapeutic purposes since they are metabolically broken down too rapidly by various enzymatic processes. All structural modifications are designed to increase their duration of effectiveness as well as their selectivity of efficacy.

SUMMARY OF THE INVENTION

It is an object of this invention to provide structurally modified prostaglandin analogs having such improved properties.

Upon further study of the specification and appended claims, further objects and advantages of this invention will become apparent to those skilled in the art.

These objects have been attained based on the discovery that certain novel 9-bromoprostaglandin derivatives possess an excellent specificity of activity, and a better efficacy and longer duration of effectiveness than natural prostaglandins and are suitable, in particular, for oral administration.

The invention thus concerns 9-bromoprostane derivatives of Formula (I)

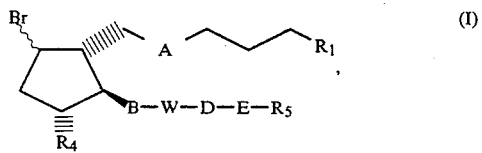

wherein
the 9-bromine atom can be in the $\alpha$- or $\beta$-position;
$R_1$ is $CH_2OH$ or

wherein $R_2$ is hydrogen or alkyl, cycloalkyl, aryl, or a heterocyclic residue; or $R_1$ is

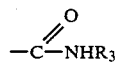

wherein $R_3$ is an acid residue (an acyl group) or $R_2$; and
A is —$CH_2$—$CH_2$— or cis—CH=CH—;
B is —$CH_2$—$CH_2$—, trans—CH=CH—, or C≡C—;
W is a free or functionally modified hydroxymethylene group or a free or functionally modified

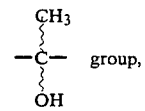

wherein the OH-groups can be in the $\alpha$- or $\beta$-position;
D and E together represent a direct bond; or
D is a straight-chain, branched-chain, or cyclic alkylene group of 1–10 carbon atoms, optionally substituted by fluorine atom(s), and
E is an oxygen atom, a sulfur atom, a direct bond, a —C≡C— bond, or —$CR_6$=$CR_7$—, wherein $R_6$ and $R_7$ are different from each other and each is hydrogen, chlorine, or $C_1$-$C_4$-alkyl;
$R_4$ is a free or functionally modified hydroxy group; and
$R_5$ is hydrogen, alkyl, halosubstituted alkyl, cycloalkyl, optionally substituted aryl, or a heterocyclic group;
and, when $R_2$ is hydrogen, the salts thereof with physiologically compatible bases.

DETAILED DISCUSSION

Suitable alkyl groups $R_2$ include straight chain or branched alkyl groups of 1–10 carbon atoms, such as, for example, methyl, ethyl, propyl, butyl, isobutyl, tert-butyl, pentyl, neopentyl, hexyl, heptyl, or decyl. The alkyl groups $R_2$ can optionally be mono- to polysubstituted by halogen atoms (F, Cl, Br), $C_{1-4}$-alkoxy groups, optionally substituted aryl or aroyl groups, di-$C_{1-4}$-alkylamino or tri-$C_{1-4}$-alkylammonium groups. Single substitution is preferred. The aryl portions of the optionally substituted aryl or aroyl groups are as defined below for the aryl $R_2$ groups per se. Examples of suitable substituents include fluorine, chlorine, bromine, phenyl, dimethylamino, diethylamino, methoxy, ethoxy, etc. Preferred alkyl groups $R_2$ are those of 1–4 carbon atoms, such as, for example, methyl, ethyl, propyl, dimethylaminopropyl, isobutyl, or butyl.

Suitable aryl groups $R_2$ include substituted as as well as unsubstituted aryl groups, e.g., phenyl, 1-naphthyl, and 2-naphthyl, each of which can be substituted by 1–3 halogen atoms, phenyl, 1–3 alkyl groups of 1–4 carbon atoms each, chloromethyl, fluoromethyl, trifluoromethyl, carboxy, hydroxy, or alkoxy of 1–4 carbon atoms. Substitution in the 3- and 4-positions on the phenyl ring is preferred, e.g. by fluorine, chlorine, alkoxy, or trifluoromethyl, or in the 4-position by hydroxy.

Suitable cycloalkyl groups $R_2$ contain 3–10, preferably 5 or 6 carbon atoms in the ring. The rings can be substituted by alkyl groups of 1–4 carbon atoms. Examples include cyclopentyl, cyclohexyl, methylcyclohexyl, and adamantyl.

Suitable heterocyclic groups $R_2$ are 5- and 6-membered heterocycles containing at least one hetero atom, preferably one, preferably nitrogen, oxygen, or sulfur, and, preferably, aromatic heterocycles, the remaining atoms being C-atoms. Examples include 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, and others.

Suitable acid residues $R_3$ include all physiologically acceptable acid residues. Preferred acids are organic carboxylic acids and sulfonic acids of 1–15 carbon atoms and belonging to the aliphatic, cycloaliphatic, aromatic, aromatic-aliphatic, and heterocyclic series. The acids are usually hydrocarbon based but the heterocyclic and other non-hydrocarbon acids are fully equivalent as are the substituted analogs of all of these. Thus, these acids can be saturated, unsaturated and/or polybasic and/or can be substituted in the usual way. Examples of substituents include alkyl, hydroxy, alkoxy, oxo, or amino groups or halogen atoms. The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid. Especially preferred acyl residues are those of up to 10 carbon atoms. Examples of sulfonic acids include alkanesulfonic acids of 1–10 carbon atoms, such as, for example, methanesulfonic acid, ethanesulfonic acid, isopropanesulfonic acid, and butanesulfonic acid, as well as $\beta$-chloroethanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis($\beta$-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acid.

The hydroxy groups in W and $R_4$ can be functionally modified, for example by etherification or esterification, wherein the modified hydroxy group in W can likewise be in the $\alpha$- or $\beta$-position. Free hydroxy groups are preferred.

All residues known to those skilled in the art can be used as the ether and acyl residues. Preferred are ether residues which can be readily split off, such as, for example, the tetrahydropyranyl, tetrahydrofuranyl, $\alpha$-ethoxyethyl, trimethylsilyl, dimethyl-tert-butylsilyl, and tribenzylsilyl residues. Suitable acyl residues are the same as those recited for $R_3$ as organic carboxylic acids; particularly useful ones include, for example, acetyl, propionyl, butyryl, and benzoyl.

Suitable aliphatic groups, e.g., alkyl and alkenyl groups $R_5$ are straight-chain and branched alkyl residues of 1–10 carbon atoms and alkenyl residues of 2–10, especially 1–6 and 2–6 carbon atoms, respectively, which can optionally be substituted by optionally substituted aryl, e.g., phenyl (e.g., substituted as defined for $R_2$ aryl groups above), alkyl of 1–4 carbon atoms, or halogen (F, Cl, Br). Examples include methyl, ethyl, propyl, isobutyl, tert-butyl, pentyl, hexyl, heptyl, octyl, butenyl, isobutenyl, propenyl, pentenyl, hexenyl, as well as benzyl; and, when D and E combined mean a direct bond, these can also include alkynyl of 2–6 carbon atoms substituted, if desired, in the 1-position by fluorine or $C_1$–$C_4$-alkyl. Suitable Alkynyl residues include ethynyl, propyn-1-yl, propyn-2-yl, 1-methylpropyn-2-yl, 1-fluoropropyn-2-yl, 1-ethylpropyn-2-yl, 1-fluorobutyn-2-yl, butyn-2-yl, butyn-3-yl, 1-methylbutyn-3-yl, 1-methylpentyn-3-yl, 1-fluoropentyn-3-yl, 1-methylpentyn-2-yl, 1-fluoropentyn-2-yl, 1-methylpentyn-4-yl, 1-fluoropentyn-4-yl, hexyn-1-yl, 1-methylhexyn-2-yl, 1-fluorohexyn-2-yl, 1-methylhexyn-3-yl, 1-methylhexyn-4-yl, hexyn-3-yl, 1,1-dimethylpropyn-2-yl, 1,1-dimethylbutyn-3-yl, 1,1-dimethylpentyn-3-yl, 1,1-dimethylpentyn-4-yl, 1,1-dimethylhexyn-3-yl, 1,1-dimethylhexyn-4-yl, etc. Suitable halogen substituents for the alkyl and alkenyl groups $R_5$ include bromine, chlorine, and fluorine. Chlorine and fluorine are preferred.

Suitable cycloalkyl groups $R_5$ can have 3–10, preferably 3–6 carbon atoms in the ring. The rings can be substituted by alkyl groups of 1–4 carbon atoms. Examples include cyclopropyl, cyclobutyl, cyclopentyl, cyclohexyl, methylcyclohexyl, and adamantyl.

Examples of substituted and/or unsubstituted aryl groups $R_5$ are those described above for $R_2$, e.g., phenyl, 1-naphthyl, and 2-naphthyl, each of which can be substituted by 1–3 halogen atoms, phenyl groups, 1–3 alkyl groups of 1–4 carbon atoms each, chloromethyl, fluoromethyl, trifluoromethyl, carboxy, $C_{1-4}$-alkoxy, or hydroxy. Substitution in the 3- and 4-positions on the phenyl ring, for example by fluorine, chlorine, alkoxy, or trifluoromethyl, or in the 4-position by hydroxy is preferred.

Suitable heterocyclic groups $R_5$ are 5- and 6-membered heterocycles containing at least one hetero atom, preferably one, preferably nitrogen, oxygen, or sulfur, and, preferably, aromatic heterocydes, the remaining atoms being C-atoms. Examples include 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, and others.

Suitable alkylene groups D (i.e., aliphatic groups) can be straight-chain or branched, cyclic, saturated or unsaturated alkylene residues, e.g., alkylene or alkenylene or the cyclic counterparts, preferably saturated residues of 1–10, especially 1–5 carbon atoms, all of which can optionally be substituted by fluorine atoms. Examples include methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyltetramethylene, 1-methyltrimethylene, 1-methylenethylene, 1-methylenetetramethylene, 2-methyltrimethylene, 2-methyltetramethylene, 1,1-trimethylenethylene, 1,2-methylenethylene. If a double bond is present, the bond is usually in the 2-, 3-, or 4-position of the alkylene residue.

Suitable $R_6$ and $R_7$ alkyl groups include those mentioned above for $R_1$ which have 1–4 C-atoms.

All conventional inorganic and organic bases are suitable for the formation of physiologically compatible salts as known to those skilled in the art. Examples include alkali metal hydroxides, such as sodium and potassium hydroxide, alkaline earth metal hydroxides, such as calcium hydroxide, ammonia, amines such as ethanolamine, diethanolamine, triethanolamine, N-methylglucamine, morpholine, tris(hydroxymethyl)methylamine, etc.

The present invention furthermore relates to a process for the preparation of the 9-bromoprostane derivatives of Formula (I), comprising, in a manner known per se, brominating a compound of Formula (II)

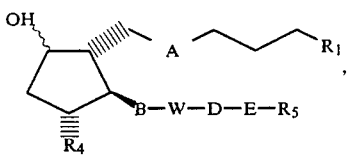 (II)

wherein
the OH-group can be in the α- or β-position,
R₁ is the residue C(O)OR₂ or C(O)NHR₃ (wherein R₂, except for the hydrogen embodiment, and R₃ are as defined above); and
A, B, D, E, and R₅ are as defined above; and
free OH-groups in R₄ and W are blocked, using the reagent tetrabromomethane/triphenylphosphine and, if desired, subsequently, in any desired sequence, liberating blocked hydroxy groups and/or etherifying or esterifying free hydroxy groups and/or hydrogenating double bonds and/or saponifying an esterified carboxy group (R₁=C(O)OR₂ and/or correcting a free carboxy group (R₂=H) into an amide (R=C(O)NHR₃) and/or reducing a free or esterified carboxy group (R₁=C(O)OR₂).

The reaction of the compounds of Formula (II) to form the compounds of Formula (I) with tetrabromomethane and triphenylphosphine can be conducted in an inert solvent such as, for example, dimethylformamide, dimethylacetamide, acetonitrile, methylene chloride, etc., at temperatures of 0° to 80° C., preferably 20°–45° C., in the presence of a base, such as, for example, pyridine, triethylamine, etc.

If an alcohol of Formula (II) with a β-positioned 9-hydroxy group is being used, compounds are obtained corresponding to Formula (I) and having a bromine atom in the 9α-position; if an alcohol is used having an α-positioned hydroxy group, then compounds are produced with a bromine atom in the 9β-position.

Reduction to produce compounds of Formula (I) wherein R₁ is —CH₂OH is conducted with a reducing agent suitable for the reduction of esters or carboxylic acids, such as, for example, lithium aluminum hydride, diisobutyl aluminum hydride, etc. Suitable solvents include diethyl ether, tetrahydrofuran, dimethoxyethane, toluene, etc. The reduction takes place at temperatures of −30° up to the boiling temperature of the solvent employed, preferably at 0°–30° C.

The functionally modified hydroxy groups can be liberated according to conventional methods. For example, hydroxy blocking groups, such as, e.g., the tetrahydropyranyl residue, are split off in an aqueous solution of an organic acid, such as, for example, oxalic acid, acetic acid, propionic acid, and others, or in an aqueous solution of an inorganic acid, such as, for example, hydrochloric acid. To enhance solubility, a water-miscible, inert organic solvent is suitably added. Organic solvents which can be used are, for example, alcohols, such as methanol and ethanol, and ethers, such as dimethoxyethane, dioxane, and tetrahydrofuran. Tetrahydrofuran is employed with preference. The splitting-off step is preferably effected at temperatures of between 20° and 80° C.

The acyl groups are saponified, for example, with alkali or alkaline earth metal carbonates or hydroxides in an alcohol or in the aqueous solution of an alcohol. Suitable alcohols are aliphatic alcohols, such as, for example, methanol, ethanol, butanol, etc., preferably methanol. Alkali metal carbonates and hydroxides include potassium and sodium salts. The potassium salts are preferred.

Examples of suitable alkaline earth metal carbonates and hydroxides are calcium carbonate, calcium hydroxide, and barium carbonate. The reaction takes place at −10° C. to +70° C., preferably at +25° C.

The introduction of the ester group C(O)OR₂ for R₁ wherein R₂ is an alkyl group of 1–10 carbon atoms takes place according to methods known to those skilled in the art. The 1-carboxy compounds are reacted, for example, with diazohydrocarbons in a manner known per se. The esterification with diazohydrocarbons takes place, for instance, by mixing a solution of the diazohydrocarbon in an inert solvent, preferably in diethyl ether, with the 1-carboxy compound in the same or in another inert solvent, such as, for example, methylene chloride. After the reaction is completed within 1–30 minutes, the solvent is removed, and the ester is purified in the usual way. Diazoalkanes are either known or can be prepared according to conventional methods (Org. Reactions vol. 8: 389–394 [1954]).

The introduction of the ester group C(O)OR₂ for R₁ wherein R₂ is a substituted or unsubstituted aryl group also takes place by means of methods known to persons skilled in the art. For example, the 1-carboxy compounds are reacted with dicyclohexylcarbodiimide in the presence of a suitable base, e.g., pyridine, dimethylaminopyridine (DMAP), triethylamine, etc. in an inert solvent with the corresponding aryl-hydroxy compounds. Suitable solvents include methylene chloride, ethylene chloride, chloroform, ethyl acetate, tetrahydrofuran, preferably chloroform. The reaction is conducted at temperatures of between −30° and −50° C., preferably at 10° C.

If C=C-double bonds present in the primary product are to be reduced, hydrogenation is carried out according to conventional methods.

The hydrogenation of the 5,6-double bond takes place conventionally at low temperatures, preferably at about −20° C., in a hydrogen atmosphere in the presence of a noble metal catalyst. A suitable catalyst is, for example, 10% palladium on charcoal.

If the 5,6- as well as the 13,14-double bonds are hydrogenated, the process is conducted at a higher temperature, for example at about 20° C.

The prostaglandin derivatives of Formula (I) wherein R₂ is a hydrogen atom can be converted into a salt with suitable amounts of the corresponding inorganic bases under conventional neutralization procedures. For example, if the corresponding PG acids are dissolved in water containing the stoichiometric quantity of the base, the solid inorganic salt is obtained after evaporation of the water or after adding a water-miscible solvent, e.g., alcohol or acetone.

For the production of an amine salt, which process also takes place in the usual way, the PG acid is dissolved, for example, in a suitable solvent, e.g., ethanol, acetone, diethyl ether, acetonitrile, or benzene, and at least the stoichiometric amount of the amine is added to this solution. During this step, the salt is ordinarily produced in the solid form or is isolated as usual after evaporation of the solvent.

The introduction of the amide group C(O)NHR₃ for R₁ also takes place according to methods known to those skilled in the art. The carboxylic acids of Formula (I) (R₂=H) are first converted into the mixed anhydride in the presence of a tertiary amine, e.g., triethylamine, with the use of isobutyl chloroformate. The mixed anhydride is reacted with the alkali metal salt of the corresponding amide or with ammonia (R₃=H) or with the corresponding amine in an inert solvent or solvent mixture, such as, for example, tetrahydrofuran, dimethoxyethane, dimethylformamide, hexamethylphosphoric triamide, at temperatures of between −30° and +60° C., preferably at 0°-30° C.

Another possibility for introducing the amide group C(O)NHR₃ for R₁, wherein R₃ is an acid residue, is to react a 1-carboxylic acid of Formula (I) (R₂=H) wherein free hydroxy groups are optionally blocked intermediarily, with compounds of Formula (III)

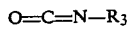  (III)

wherein R₃ is as defined above.

The reaction of the compound of Formula (I) (R₂=H) with an isocyanate of Formula (III) likewise takes place conventionally with the addition of a tertiary amine, such as, for example, triethylamine or pyridine. The reaction can be conducted without a solvent or in an inert solvent, preferably acetonitrile, tetrahydrofuran, acetone, dimethylacetamide, methylene chloride, diethyl ether, toluene, at temperatures of between −80° and 100° C., preferably at 0°-30° C.

If the starting compound has OH-groups in the prostane residue, these OH-groups are also reacted. If, in the end, products are desired containing free hydroxy groups in the prostane moiety, then starting compounds are suitably employed wherein these groups are blocked intermediarily, preferably by readily cleavable ether or acyl residues.

The compounds of Formula (II) serving as starting materials can be prepared, for example, by conventionally reducing a ketone of Formula (IV)

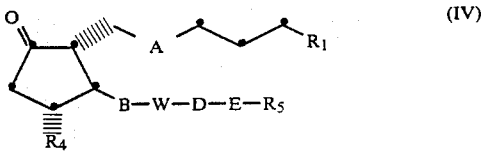  (IV)

wherein
R₁ is C(O)OR₂ or C(O)NHR₃ and
A, B, D, E, and R₅ are as defined above, and
free OH-groups in R₄ and W are blocked, with sodium borohydride, lithium tris(tert-butoxy)aluminum hydride, etc., and, optionally, thereafter conventionally separating the epimeric 9α- and 9β-positioned hydroxy compounds of Formula (II). Like the compounds of Formula (II), the compounds of Formula (III) are all known or readily preparable by fully conventional methods.

As compared with PGE derivatives, the novel 9-bromoprostaglandins of this invention are distinguished by greater stability.

The novel 9-bromoprostane derivatives of this invention are valuable pharmacological agents since they exhibit, with a similar spectrum of activity, a substantially improved effectiveness (higher specificity) and, above all, substantially prolonged efficacy than the corresponding, natural prostaglandins.

The novel prostaglandin analogs have a strong luteolytic effect, i.e., for triggering luteolysis, substantially lower doses are required than for the corresponding, natural prostaglandins.

Also, for triggering abortions, expecially upon oral or intravaginal administration, substantially lower quantities of the novel prostaglandin analogs are necessary as compared with the natural prostaglandins.

When recording isotonic uterine contraction on anesthetized rats and on the isolated rat uterus, it is found that the compounds of this invention are substantially more efficacious and that their effects are of a longer duration than for the natural prostaglandins.

The novel prostaglandin derivatives are suitable, after a single enteral or parenteral administration, for inducing menstruation or interrupting pregnancy. They are furthermore suitable for synchronizing the sexual cycle in female mammals, such as rabbits, cattle, horses, pigs, etc. Furthermore, the prostaglandin derivatives of the present invention are suitable for cervix dilation as a preparation for diagnostic or therapeutic interventions.

The high tissue specificity of the compounds of this invention as regards antifertility activity is demonstrated in studies on other smooth-muscle organs, e.g., on the guinea pig ileum or on the isolated rabbit trachea, where a substantially lesser stimulation can be observed than caused by the natural prostaglandins. The compounds of this invention also have bronchospasmolytic activity. Besides, they reduce swelling of the nasal mucous membrane.

The active agents of this invention inhibit gastric acid secretion, show a cytoprotective and ulcer-healing effect, and thus counteract the undesirable consequences of nonsteroidal antiinflammatory agents (prostaglandin synthesis inhibitors). They also have cytoprotective effects on the liver as well as the pancreas.

Several of the compounds show blood-pressure-lowering effects, a regulating effect on cardiac arrhythmias, and an inhibitory effect on platelet aggregation, with the ensuing conventional usage possibilities.

The novel prostaglandins can also be employed in combination, for example, with β-blockers and diuretics.

The preferred dose of the compounds, if administered to human patients, is 1-1,5000 μg/kg/day.

For medical use, the active agents can be converted into a form suitable for inhaling, or for oral, parenteral, or local (e.g., vaginal) administration. Suitably, aerosol solutions are prepared for inhalation purposes. Tablets, dragees, or capsules are suitable, for example, for oral administration. For parenteral administration, sterile, injectable aqueous or oily solutions are utilized. Suppositories are suitable and customary, for example, for vaginal administration. Thus, the invention also concerns medicinal agents based on the compounds of Formula I and the usual auxiliary agents and excipients.

The active agents of this invention can be utilized, in conjunction with the auxiliary compounds known and customary in galenic pharmacy, for example for the production of preparations for triggering abortion, for cycle regulation, for induction of labor, or for the treatment of hypertonia. For this purpose, but also for all other applications, the unit preparations can contain 0.01-100 mg of the active compound.

The pharmacologically active compounds of this invention can be processed in accordance with conventional methods of galenic pharmacy to produce medicinal agents, especially for oral administration to mammals, including humans. Conventional excipients are pharmaceutically acceptable organic or inorganic carrier substances suitable for parenteral, enteral or topical application which do not deleteriously react with the active compounds. Suitable pharmacologically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir, or the like can be used wherein a sweetened vehicle is employed. Sustained release compositions can be formulated including those wherein the active compound is protected with differentially degradable coatings, e.g., by microencapsulation, multiple coatings, etc.

The administration of the compounds of this invention is fully analogous to that of the known PG agents such as PGE.

The novel protaglandin analogs of this invention are substantially more selective with regard to potency, as compared with known PG analogs, in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5Z,13E)-(9R,11R,15R)-9-Bromo-11,15-dihydroxy-16-phenoxy-17,18,19,20-tetranor-5,13-prostadienoic Acid Methyl Ester A solution of 1.15 g of (5Z,13E)-(9S,11R,15R)-9-hydroxy-11,15-bis(tetrahydropyran-2-yloxy)-16-phenoxy-17,18,19,20-tetranor-5,13-prostadienoic acid methyl ester, 772 mg of triphenylphosphine, 0.3 g of pyridine, and 1.25 g of tetrabromomethane in 18 ml of acetonitrile is stirred for 27 hours at 22° C. The solution is then diluted with 50 ml of water, extracted three times with a mixture of ether/hexane (1+1), the organic extract is washed with water, dried over magnesium sulfate, and evaporated under vacuum. Chromatography of the evaporation residue on silica gel yields, with hexane/ether (4+1), 690 mg of (5Z,13E)-(9R,11R,15R)-9-bromo-11,15-bis(tetrahydropyran-2-yloxy)-16-phenoxy-17,18,19,20-tetranor-5,13-prostadienoic acid methyl ester.

IR (CHCl$_3$): 2940, 2856, 1731, 1600, 1588, 1495, 972 cm$^{-1}$.

To split off tetrahydropyranyl ether, 690 mg of the above-produced compound is agitated for 16 hours at 22° C. with 30 ml of a mixture of acetic acid/water/tetrahydrofuran (65+35+10) and then evaporated under vacuum. The residue is purified by chromatography on silica gel. With toluene/isopropanol (98+2), 225 mg of the title compound is obtained as a colorless oil.

IR: 3600, 3420 (broad), 2930, 2857, 1730, 1599, 1494, 970 cm$^{-1}$.

EXAMPLE 2

(5Z,13E)-(9S,11R,15R)-9-Bromo-11,15-dihydroxy-16-phenoxy-17,18,19,20-tetranor-5,13-prostadienoic Acid Methyl Ester A solution of 574 mg of (5Z,13E)-(9R,11R,15R)-9-hydroxy-11,15-bis(tetrahydropyran-2-yloxy)-16-phenoxy-17,18,19,20-tetranor-5,13-prostadienoic acid methyl ester, 0.52 of tetrabromomethane, and 0.125 g of pyridine in 7.5 ml of acetonitrile is combined with 386 mg of triphenylphosphine. The mixture is stirred for 24 hours at 22° C., then diluted with water, extracted three times with a mixture of ether/hexane (1+1), the organic extract is washed with water, dried over magnesium sulfate, and evaporated under vacuum. After chromatography of the evaporation residue on silica gel, hexane/ether (7+3) yields 380 mg of (5Z,13E)-(9S,11R,15R)-9-bromo-11,15-bis(tetrahydropyran-2-yloxy)-16-phenoxy-17,18,19,20-tetranor-5,13-prostadienoic acid methyl ester.

IR: 2940, 2857, 1730, 1600, 1588, 1494, 970 cm$^{-1}$.

To split off tetrahydropyranyl ether, 380 mg of the above-produced 9α-bromine compound is stirred for 16 hours at 22° C. with 18 ml of a solution of acetic acid/water/tetrahydrofuran (65+35+10) and then evaporated under vacuum. The residue is purified by chromatography on silica gel. With ethyl acetate/hexane (7+3), 220 mg of the title compound is obtained as an oil.

IR: 3590, 3420 (broad), 2930, 2860, 1730, 1600, 1589, 1495, 971 cm$^{-1}$.

EXAMPLE 3

(13E)-(9R,11R,15R)-9-Bromo-11,15-dihydroxy-16-phenoxy-17,18,19,20-tetranor-13-prostenoic Acid Methyl Ester Analogously to Example 1, 0.65 g of (13E)-(9S,11R,15R)-9-hydroxy-11,15-bis(tetrahydropyran-2-yloxy)-16-phenoxy-17,18,19,20-tetranor-13-prostenoic acid methyl ester yields 310 mg of (13E)-(9R,11R,15R)-9-bromo-11,15-bis(tetrahydropyran-2-yloxy)-16-phenoxy-17,18,19,20-tetranor-13-prostenoic acid methyl ester.

IR: 2942, 2857, 1731, 1600, 1588, 971 cm$^{-1}$.

After the blocking groups have been split off in accordance with Example 1, 98 mg of the title compound is produced as a colorless oil.

IR: 3610, 3410 (broad), 2931, 2858, 1731, 1599, 1588, 971 cm$^{-1}$.

EXAMPLE 4

(13E)-(9S,11R,15R)-9-Bromo-11,15-dihydroxy-16-phenoxy-17,18,19,20-tetranor-13-prostenoic Acid Methyl Ester Analogously to Example 2, 300 mg of (13E)-(9R,11R,15R)-9-hydroxy-11,15-bis(tetrahydropyran-2-yloxy)-16-phenoxy-17,18,19,20-tetranor-13-prostenoic acid methyl ester yields 195 mg of (13E)-(9S,11R,15R)-9-bromo-11,15-bis(tetrahydropyran-2-yloxy)-16-phenoxy-17,18,19,20-tetranor-13-prostenoic acid methyl ester.

IR: 2940, 2858, 1730, 1600, 1588, 1494, 970 cm$^{-1}$.

After the blocking groups have been split off according to Example 2, 110 mg of the title compound is obtained as a colorless oil.

IR: 3600, 3400 (broad), 2930, 2858, 1730, 1599, 1589, 970 cm$^{-1}$.

EXAMPLE 5

(5Z,13E)-(9R,11R,15R)-9-Bromo-11,15-dihydroxy-16,16-dimethyl-5,13-prostadienoic Acid Methyl Ester In analogy to Example 1, 0.7 g of (5Z,13E)-(9S,11R,15R)-16,16-dimethyl-9-hydroxy-11,15-bis(tetrahydropyran-2-yloxy)-5,13-prostadienoic acid methyl ester produces 0.38 g of (5Z,13E)-(9R,11R,15R)-9-bromo-11,15-bis(tetrahydropyran-2-yloxy)-16,16-dimethyl-5,13-prostadienoic acid methyl ester.

IR: 2942, 2858, 1732, 972 cm$^{-1}$.

After the blocking groups have been split off as described in Example 1, 120 mg of the title compound is produced as a colorless oil.

IR: 3600, 3400 (broad), 2935, 1732, 973 cm$^{-1}$.

EXAMPLE 6

(5Z,13E)-(9S,11R,15R)-9-Bromo-11,15-dihydroxy-16,16-dimethyl-5,13-prostadienoic Acid Methyl Ester In analogy to Example 2, 190 mg of (5Z,13E)-(9R,11R,15R)-16,16-dimethyl-9-hydroxy-11,15-bis(tetrahydropyran-2-yloxy)-5,13-prostadienoic acid methyl ester gives 108 mg of (5Z,13E)-(9S,11R,15R)-9-bromo-16,16-dimethyl-11,15-bis(tetrahydropyran-2-yloxy)-5,13-prostadienoic acid methyl ester.

IR: 2943, 2860, 1733, 973 cm$^{-1}$.

After the blocking groups have been split off in accordance with Example 2, 65 mg of the title compound is obtained as a colorless oil.

IR: 3610, 3410 (broad), 2935, 1733, 973 cm$^{-1}$.

EXAMPLE 7

(5Z,13E)-(9R,11R,15S,16RS)-9-Bromo-11,15-dihydroxy-16-methyl-5,13-prostadienoic Acid Methyl Ester In analogy to Example 1, 0.9 g of (5Z,13E)-(9S,11R,15S,16RS)-9-hydroxy-16-methyl-11,15-bis(tetrahydropyran-2-yloxy)-5,13-prostadienoic acid methyl ester gives 0.43 g of (5Z,13E)-(9R,11R,15S,16RS)-9-bromo-16-methyl-11,15-bis(tetrahydropyran-2-yloxy)-5,13-prostadienoic acid methyl ester.

IR: 2940, 2858, 1731, 971 cm$^{-1}$.

After the blocking groups have been split off according to Example 1, 138 mg of the title compound is produced as a colorless oil.

IR: 3600, 3420 (broad), 2936, 2860, 1731, 971 cm$^{-1}$.

EXAMPLE 8

(5Z,13E)-(9S,11R,15S,16RS)-9-Bromo-11,15-dihydroxy-16-methyl-5,13-prostadienoic Acid Methyl Ester In analogy to Example 2, 280 mg of (5Z,13E)-(9R,11R,15S,16RS)-9-hydroxy-16-methyl-11,15-bis(tetrahydropyran-2-yloxy)-5,13-prostadienoic acid methyl ester yields 165 mg of (5Z,13E)-(9S,11R,15S,16RS)-9-bromo-16-methyl-11,15-bis(tetrahydropyran-2-yloxy)-5,13-prostadienoic acid methyl ester.

IR: 2940, 2860, 1732, 972 cm$^{-1}$.

After the blocking groups have been split off according to Example 2, 90 mg of the title compound is produced as a colorless oil.

IR: 3620, 3400 (broad), 2935, 2862, 1732, 972 cm$^{-1}$.

EXAMPLE 9

(5Z,13E)-(9R,11R,15RS)-9-Bromo-11,15-dihydroxy-15-methyl-5,13-prostadienoic Acid Methyl Ester Analogously to Example 1, 1.2 g of (5Z,13E)-(9S,11R,15RS)-9-hydroxy-15-methyl-11,15-bis(tetrahydropyran-2-yloxy)-5,13-prostadienoic acid methyl ester gives 680 mg of (5Z,13E)-(9R,11R,15RS)-9-bromo-15-methyl-11,15-bis(tetrahydropyran-2-yloxy)-5,13-prostadienoic acid methyl ester.

IR: 1730, 974 cm$^{-1}$.

After the blocking groups have been split off in accordance with Example 1, 260 mg of the title compound is obtained as a colorless oil.

IR: 3620, 3420 (broad), 2938, 1730, 974 cm$^{-1}$.

EXAMPLE 10

(13E)-(9R,11R,15S,16RS)-9-Bromo-11,15-dihydroxy-16,19-dimethyl-13,18-prostadienoic Acid Methyl Ester Analogously to Example 1, 0.8 g of (13E)-(9S,11R,15S,16RS)-16,19-dimethyl-9-hydroxy-11,15-bis(tetrahydropyran-2-yloxy)-13,18-prostadienoic acid methyl ester gives 480 mg of (13E)-(9R,11R,15S,16RS)-9-bromo-16,19-dimethyl-11,15-bis(tetrahydropyran-2-yloxy)-13,18-prostadienoic acid methyl ester.

IR: 2962, 1731, 972 cm$^{-1}$.

After the blocking groups have been split off as disclosed in Example 1, 220 mg of the title compound is obtained as a colorless oil.

IR: 3610, 3410 (broad), 2933, 2856, 1731, 972 cm$^{-1}$.

EXAMPLE 11

(13E)-(9S,11R,15S,16RS)-9-Bromo-11,15-dihydroxy-16,19-dimethyl-13,18-prostadienoic Acid Methyl Ester In analogy to Example 2, 0.38 g of (13E)-(9R,11R,15S,16RS)-16,19-dimethyl-9-hydroxy-11,15-bis(tetrahydropyran-2-yloxy)-13,18-prostadienoic acid methyl ester yields 240 mg of (13E)-(9S,11R,15S,16RS)-9-bromo-16,19-dimethyl-11,15-bis(tetrahydropyran-2-yloxy)-13,18-prostadienoic acid methyl ester.

IR: 2960, 1730, 970 cm$^{-1}$.

After splitting off the blocking groups according to Example 2, 160 mg of the title compound is produced as a colorless oil.

IR: 3600, 3400 (broad), 2935, 2855, 1730, 970 cm$^{-1}$.

EXAMPLE 12

(5Z,13E)-(9R,11R,15R)-9-Bromo-11,15-dihydroxy-16,16,19-trimethyl-5,13,18-prostatrienoic Acid Methyl Ester Analogously to Example 1, 0.65 g of (5Z,13E)-(9S,11R,15R)-9-hydroxy-11,15-bis(tetrahydropyran-2-yloxy)-16,16,19-trimethyl-5,13,18-prostatrienoic acid methyl ester yields 0.38 g of (5Z,13E)-(9R,11R,15R)-9-bromo-11,15-bis(tetrahydropyran-2-yloxy)-16,16,19-trimethyl-5,13,18-prostatrienoic acid methyl ester.

IR: 2962, 1732, 970 cm$^{-1}$.

After the blocking groups have been split off according to Example 1, 0.18 g of the title compound is obtained as a colorless oil.

IR: 3600, 3400 (broad), 2942, 2850, 1732, 970 cm$^{-1}$.

EXAMPLE 13

(5Z,13E)-(9S,11R,15R)-9-Bromo-11,15-dihydroxy-16,16,19-trimethyl-5,13,18-prostatrienoic Acid Methyl Ester Analogously to Example 2, 0.7 g of (5Z,13E)-(9R,11R,15R)-9-hydroxy-11,15-bis(tetrahydropyran-2-yloxy)-16,16,19-trimethyl-5,13,18-prostatrienoic acid methyl ester gives 0.48 g of (5Z,13E)-(9S,11R,15R)-9-bromo-11,15-bis(tetrahydropyran-2-yloxy)-16,16,19-trimethyl-5,13,18-prostatrienoic acid methyl ester.

IR: 2960, 1733, 972 cm$^{-1}$.

After the blocking groups have been split off according to Example 2, 0.36 g of the title compound is obtained as a colorless oil.

IR: 3600, 3410 (broad), 2941, 2853, 1733, 972 cm$^{-1}$.

EXAMPLE 14

(5Z,13E)-(9R,11R,15R)-9-Bromo-11,15-dihydroxy-16-phenoxy-17,18,19,20-tetranor-5,13-prostadienoic Acid 225 mg of the methyl ester prepared according to Example 1 is agitated for one hour with 12 ml of a solution of potassium hydroxide in ethanol and water (preparation: 2 g of potassium hydroxide is dissolved in 75 ml of ethanol and 25 ml of water). The mixture is then acidified with 10% citric acid solution to pH 4, extracted three times with methylene chloride, the organic extract is washed once with brine, dried over magnesium sulfate, and evaporated under vacuum. Chromatography of the residue on silica gel with ethyl acetate/acetic acid (99.5+0.5) as the eluent yields 168 mg of the title compound as a colorless oil.

IR: 3600, 3430 (broad), 2925, 2855, 1710, 1599, 1587, 1493, 970 cm$^{-1}$.

EXAMPLE 15

(5Z,13E)-(9S,11R,15R)-9-Bromo-11,15-dihydroxy-16-phenoxy-17,18,19,20-tetranor-5,13-prostadienoic Acid Analogously to Example 14, 0.14 g of the methyl ester prepared according to Example 2 gives 115 mg of the title compound of a waxy composition.

IR: 3590, 3400 (broad), 2930, 2853, 1710, 1599, 1588, 1492, 969 cm$^{-1}$.

EXAMPLE 16

(13E)-(9R,11R,15R)-9-Bromo-11,15-dihydroxy-16-phenoxy-17,18,19,20-tetranor-13-prostenoic Acid In analogy to Example 14, 0.19 g of the methyl ester prepared as described in Example 3 yields 0.14 g of the title compound as a colorless oil.

IR: 3600, 3400 (broad), 2932, 2853, 1709, 1599, 1588, 1492, 970 cm$^{-1}$.

EXAMPLE 17

(13E)-(9S,11R,15R)-9-Bromo-11,15-dihydroxy-16-phenoxy-17,18,19,20-tetranor-13-prostenoic Acid In analogy to Example 14, 0.3 g of the methyl ester prepared according to Example 4 gives 0.24 g of the title compound as a colorless oil.

IR: 3610, 3420 (broad), 2933, 2852, 1710, 1599, 1588, 1493, 971 cm$^{-1}$.

EXAMPLE 18

(5Z,13E)-(9R,11R,15R)-9-Bromo-11,15-dihydroxy-16,16-dimethyl-5,13-prostadienoic Acid In analogy to Example 14, 0.24 g of the methyl ester prepared as described in Example 5 yields 0.18 g of the title compound as a colorless oil.

IR: 3600, 3410 (broad), 2935, 1709, 973 cm$^{-1}$.

EXAMPLE 19

(5Z,13E)-(9S,11R,15R)-9-Bromo-11,15-dihydroxy-16,16-dimethyl-5,13-prostadienoic Acid In analogy to Example 14, 0.14 g of the methyl ester produced as per Example 6 gives 0.10 g of the title compound as a colorless oil.

IR: 3600, 3410 (broad), 2938, 1710, 974 cm$^{-1}$.

EXAMPLE 20

(5Z,13E)-(9R,11R,15S,16RS)-9-Bromo-11,15-dihydroxy-16-methyl-5,13-prostadienoic Acid Analogously to Example 14, 0.14 g of the methyl ester prepared as disclosed in Example 7 yields 0.11 g of the title compound as a colorless oil.

IR: 3600, 3405 (broad), 2940, 1710, 978 cm$^{-1}$.

EXAMPLE 21

(5Z,13E)-(9S,11R,15S,16RS)-9-Bromo-11,15-dihydroxy-16-methyl-5,13-prostadienoic Acid Analogously to Example 14, 0.2 g of the methyl ester produced in accordance with Example 8 gives 0.16 g of the title compound as a colorless oil.

IR: 3600, 3405 (broad), 2938, 1710, 976 cm$^{-1}$.

EXAMPLE 22

(5Z,13E)-(9R,11R,15RS)-9-Bromo-11,15-dihydroxy-15-methyl-5,13-prostadienoic Acid In analogy to Example 14, 0.25 g of the methyl ester produced according to Example 9 yields 0.20 g of the title compound as a colorless oil.

IR: 3600, 3410 (broad), 2945, 2860, 1712, 978 cm$^{-1}$.

EXAMPLE 23

(13E)-(9R,11R,15S,16RS)-9-Bromo-11,15-dihydroxy-16,19-dimethyl-13,18-prostadienoic Acid Analogously to Example 14, 0.25 g of the methyl ester prepared as described in Example 10 gives 0.20 g of the title compound as a colorless oil.

IR: 3600, 3410 (broad), 2940, 2855, 1710, 1605, 976 cm$^{-1}$.

EXAMPLE 24

(13E)-(9S,11R,15S,16RS)-9-Bromo-11,15-dihydroxy-16,19-dimethyl-13,18-prostadienoic Acid Analogously to Example 14, 0.23 g of the methyl ester prepared as disclosed in Example 11 yields 0.19 g of the title compound as a colorless oil.

IR: 3600, 3410 (broad), 2938, 2854, 1710, 1605, 976 cm$^{-1}$.

EXAMPLE 25

(5Z,13E)-(9R,11R,15R)-9-Bromo-11,15-dihydroxy-16,16,19-trimethyl-5,13,18-prostatrienoic Acid In analogy to Example 14, 0.2 g of the methyl ester produced according to Example 12 gives 0.17 g of the title compound as a colorless oil.

IR: 3600, 3410 (broad), 2945, 2852, 1708, 1603, 976 cm$^{-1}$.

EXAMPLE 26

(5Z,13E)-(9S,11R,15R)-9-Bromo-11,15-dihydroxy-16,16,19-trimethyl-5,13,18-prostatrienoic Acid In analogy to Example 14, 0.2 g of the methyl ester prepared according to Example 13 yields 0.17 g of the title compound as a colorless oil.

IR: 3610, 3410 (broad), 2948, 2850, 1710, 1604, 976 cm$^{-1}$.

EXAMPLE 27

(13E)-(9R,11R,15R)-9-Bromo-1,11,15-trihydroxy-16-phenoxy-17,18,19,20-tetranor-13-prostene At 0° C., 300 mg of lithium aluminum hydride is added under agitation in incremental portions to a solution of 250 mg of (13E)-(9R,11R,15R)-9-bromo-11,15-dihydroxy-16-phenoxy-17,18,19,20-tetranor-13-prostenoic acid methyl ester (prepared according to Example 3) in 10 ml of tetrahydrofuran. The mixture is then stirred for 30 minutes at 0° C. The excess reagent is destroyed at 0° C. by the dropwise addition of ethyl acetate, 1 ml of water and 50 ml of ether are added, and the mixture is thoroughly agitated for 3 hours at 25° C., filtered, the residue washed with ether, the ether solution dried over magnesium sulfate, and evaporated under vacuum. After chromatography of the residue on silica gel with ethyl acetate/hexane (4+1), 205 mg of the title compound is obtained as a colorless oil.

IR: 3600, 3425 (broad), 2950, 2858, 1600, 1588, 1485, 978 cm$^{-1}$.

EXAMPLE 28

(13E)-(9S,11R,15R)-9-Bromo-1,11,15-trihydroxy-16-phenoxy-17,18,19,20-tetranor-13-prostene In analogy to Example 27, 200 mg of (13E)-(9S,11R,15R)-9-bromo-11,15-dihydroxy-16-phenoxy-17,18,19,20-tetranor-13-prostenoic acid methyl ester (prepared according to Example 4) yields 150 mg of the title compound as a colorless oil.

IR: 3600, 3420 (broad), 2948, 2858, 1600, 1588, 1480, 976 cm$^{-1}$.

EXAMPLE 29

(13E)-(9R,11R,15R)-9-Bromo-11,15-dihydroxy-16-phenoxy-17,18,19,20-tetranor-13-prostenoic Acid Methylsulfonamide At −10° C., 85 mg of isobutyl chloroformate and 66 mg of triethylamine are added to a solution of 200 mg of (13E)-(9R,11R,15R)-9-bromo-11,15-dihydroxy-16-phenoxy-17,18,19,20-tetranor-13-prostenoic acid (prepared according to Example 16) in 5 ml of dimethylformamide. After 60 minutes, 280 mg of the sodium salt of methylsulfonamide (prepared from methylsulfonamide and sodium methylate) and 2 ml of hexamethylphosphoric triamide are added to the reaction mixture and the latter is agitated for 5 hours at +10° C. Thereafter, the mixture is diluted with citrate buffer (pH 4), extracted with ethyl acetate, the extract washed with salt, dried over magnesium sulfate, and evaporated under vacuum. After chromatography of the residue on silica gel with methylene chloride, 130 mg of the title compound is obtained as an oil.

IR: 3600, 3410, 2954, 2860, 1718, 1600, 1588, 976 cm$^{-1}$.

EXAMPLE 30

(13E)-(9S,11R,15R)-9-Bromo-11,15-dihydroxy-16-phenoxy-17,18,19,20-tetranor-13-prostenoic Acid Methylsulfonamide Analogously to Example 29, 100 mg of (13E)-(9S,11R,15R)-9-bromo-11,15-dihydroxy-16-phenoxy-17,18,19,20-tetranor-13-prostenoic acid (produced according to Example 17) yields 60 mg of the title compound as a colorless oil.

IR: 3600, 3405, 2956, 2860, 1718, 1601, 1588, 976 cm$^{-1}$.

EXAMPLE 31

(13E)-(9R,11R,15R)-9-Bromo-11,15-dihydroxy-16-phenoxy-17,18,19,20-tetranor-13-prostenoic Acid Amide At −10° C., 85 mg of isobutyl chloroformate and 66 mg of triethylamine are added to a solution of 200 mg of (13E)-(9R,11R,15R)-9-bromo-11,15-dihydroxy-16-phenoxy-17,18,19,20-tetranor-13-prostenoic acid in 5 ml of tetrahydrofuran. After one hour, ammonia in gas form is conducted for 15 minutes into the mixture and the latter is allowed to stand for 2 hours at −10° C. and the mixture is then diluted with water, repeatedly extracted with methylene chloride, the combined extracts are washed with brine, dried over magnesium sulfate, and evaporated under vacuum. The product is purified by chromatography on silica gel with methylene chloride, thus obtaining 140 mg of the title compound as an oil.

IR: 3600, 3450, 2958, 2840, 1668, 1608, 1590, 976 cm$^{-1}$.

EXAMPLE 32

(13E)-(9R,11R,15R)-9-Bromo-11,15-dihydroxy-16-phenoxy-17,18,19,20-tetranorprostenoic Acid Tris(hydroxymethyl)aminomethane Salt At 65° C., a solution of 55 mg of tris(hydroxymethyl)aminomethane in 0.18 ml of water is added to a solution of 200 mg of (13E)-(9R,11R,15R)-9-bromo-11,15-dihydroxy-16-phenoxy-17,18,19,20-tetranorprostenoic acid (prepared according to Example 16) in 35 ml of acetonitrile. The mixture is allowed to cool to 20° C. under stirring, decanted off from the solvent, and the residue is dried under vacuum. Yield: 175 mg of the title compound as a viscous oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 9-bromoprostane of the formula

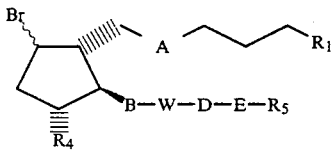

wherein the 9-bromine atom is in the α- or β-position, $R_1$ is $CH_2OH$ or $C(O)OR_2$ wherein $R_2$ is (a) hydrogen, (b) $C_{1-10}$ alkyl, (c) $C_{1-10}$ alkyl substituted by halogen; $C_{1-4}$ alkoxy; $C_{6-10}$ aryl; $C_{6-10}$ aroyl; $C_{6-10}$ aryl or $C_{6-10}$ aroyl each substituted by 1-3 halogen atoms, phenyl, 1-3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{3-10}$ cycloalkyl, (e) $C_{3-10}$ cycloalkyl substituted by $C_{1-3}$ halogen atoms, phenyl, 1-3 $C_{1-4}$ alkyl groups or a chloromethyl, fluoromethyl, trifluoromethyl carboxy, hydroxy or $C_{1-4}$ alkoxy group, or (h) an aromatic heterocycle of 5 or 6 ring atoms one of which is O, N or S, the remainder being carbon atoms; or $R_1$ is $C(O)NHR_3$ wherein $R_3$ is an acyl group of a hydrocarbon $C_{1-15}$ carboxylic or sulfonic acid or is $R_2$;

A is —$CH_2$—$CH_2$— or cis—CH=CH—;
B is —$CH_2$—$CH_2$—, trans—CH=CH—, or —C≡C—;
W is hydroxymethylene, RO-methylene,

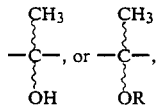

wherein OH or OR is in the α- or β- position;

R is tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;

D and E together are a direct bond, or
D is alkylene, alkenylene, cycloalkylene or cycloalkenylene, each of 1-10 carbon atoms, or one of said groups substituted by fluorine, and
E is oxygen, sulfur, a direct bond, —C≡C—, or —$CR_6$=$CR_7$—, wherein $R_6$ and $R_7$ are different from each other and each is hydrogen, chlorine, or $C_1$-$C_4$-alkyl;
$R_4$ is OH or OR; and
$R_5$ is (a) hydrogen, (b) $C_{1-10}$-alkenyl each substituted by halogen, $C_{1-4}$-alkyl, $C_{6-10}$-aryl or by $C_{6-10}$-aryl substituted by 1-3 halogen atoms, phenyl, 1-3 $C_{1-4}$ alkyl groups or a chloromethyl, fluoromethyl, trifluoromethyl, carboxy, hydroxy or $C_{1-4}$ alkoxy group; (e) when D and E together are a direct bond, $R_5$ can also be $C_{2-6}$-alkynyl or $C_{2-6}$-alkynyl substituted in the 1-position by fluorine or $C_{1-4}$-alkyl, (f) $C_{3-10}$, cycloalkyl, (g) $C_{3-10}$ cycloalkyl substituted by $C_{1-4}$ alkyl, (h) $C_{6-10}$ aryl, (i) $C_{6-10}$ aryl substituted by 1-3 halogen atoms, phenyl, 1-3 $C_{1-4}$ alkyl groups or a chloromethyl, fluoromethyl, trifluoromethyl, carboxy, hydroxy or $C_{1-4}$ alkoxy group; or (j) an aromatic heterocycle of 5 or 6 ring atoms one of which is O, N or S, the remainder being carbon atoms;

or, when $R_2$ is hydrogen, a physiologically compatible salt thereof with a base, with the proviso that the compound is not 9-deoxy-9β-bromo-16,16-dimethyl-PGF$_2$, an ester thereof or a salt thereof.

2. A compound of claim 1 wherein B—W—D—E—$R_5$ is

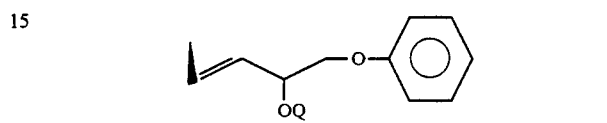

wherein Q is H or R.

3. A compound of claim 1 wherein B—W—D—E—$R_5$ is

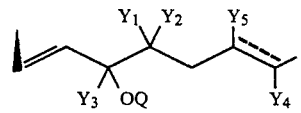

wherein Q is H or R, --- represents a single or double bond, each of $Y_1$, $Y_2$ and $Y_3$ independently is H or $CH_3$, and each of $Y_4$ and $Y_5$ independently is H or $CH_3$ with the proviso that when --- is a double bond one of $Y_4$ and $Y_5$ is H and the other is $CH_3$.

4. (5Z,13E)-(9R,11R,15R)-9-bromo-11,15-dihydroxy-16-phenoxy-17,18,19,20-tetranor-5,13-prostadienoic acid methyl ester, a compound of claim 1.

5. (5Z,13E)-(9S,11R,15R)-9-bromo-11,15-dihydroxy-16-phenoxy-17,18,19,20-tetranor-5,13-prostadienoic acid methyl ester, a compound of claim 1.

6. (13E)-(9R,11R,15R)-9-bromo-11,15-dihydroxy-16-phenoxy-17,18,19,20-tetranor-13-prostenoic acid methyl ester, a compound of claim 1.

7. (13E)-(9S,11R,15R)-9-bromo-11,15-dihydroxy-16-phenoxy-17,18,19,20-tetranor-13-prostenoic acid methyl ester, a compound of claim 1.

8. (5Z,13E)-(9S,11R,15R)-9-bromo-11,15-dihydroxy-16,16-dimethyl-5,13-prostadienoic acid methyl ester, a compound of claim 1.

9. (5Z,13E)-(9R,11R,15S,16RS)-9-bromo-11,15-dihydroxy-16-methyl-5,13-prostadienoic acid methyl ester, a compound of claim 1.

10. (5Z,13E)-(9S,11R,15S,16RS)-9-bromo-11,15-dihydroxy-16-methyl-5,13-prostadienoic acid methyl ester, a compound of claim 1.

11. (5Z,13E)-(9R,11R,15RS)-9-bromo-11,15-dihydroxy-15-methyl-5,13-prostadienoic acid methyl ester, a compound of claim 1.

12. (13E)-(9R,11R,15S,16RS)-9-bromo-11,15-dihydroxy-16,19-dimethyl-13,18-prostadienoic acid methyl ester, a compound of claim 1.

13. (13E)-(9S,11R,15S,16RS)-9-bromo-11,15-dihydroxy-16,19-dimethyl-13,18-prostadienoic acid methyl ester, a compound of claim 1.

14. (5Z,13E)-(9R,11R,15R)-9-bromo-11,15-dihydroxy-16,16,19-trimethyl-5,13,18-prostatrienoic acid methyl ester, a compound of claim 1.

15. (5Z,13E)-(9S,11R,15R)-9-bromo-11,15-dihydroxy-16,16,19-trimethyl-5,13,18-prostatrienoic acid methyl ester, a compound of claim 1.

16. (5Z,13E)-(9R,11R,15R)-9-bromo-11,15-dihydroxy-16-phenoxy-17,18,19,20-tetranor-5,13-prostadienoic acid, a compound of claim 1.

17. (5Z,13E)-(9S,11R,15R)-9-bromo-11,15-dihydroxy-16-phenoxy-17,18,19,20-tetranor-5,13-prostadienoic acid, a compound of claim 1.

18. (13E)-(9R,11R,15R)-9-bromo-11,15-dihydroxy-16-phenoxy-17,18,19,20-tetranor-13-prostenoic acid, a compound of claim 1.

19. (13E)-(9S,11R,15R)-9-bromo-11,15-dihydroxy-16-phenoxy-17,18,19,20-tetranor-13-prostenoic acid, a compound of claim 1.

20. (5Z,13E)-(9S,11R,15R)-9-bromo-11,15-dihydroxy-16,16-dimethyl-5,13-prostadienoic acid, a compound of claim 1.

21. (5Z,13E)-(9R,11R,15S,16RS)-9-bromo-11,15-dihydroxy-16-methyl-5,13-prostadienoic acid, a compound of claim 1.

22. (5Z,13E)-(9S,11R,15S,16RS)-9-bromo,11,15-dihydroxy-16-methyl-5,13-prostadienoic acid, a compound of claim 1.

23. (5Z,13E)-(9R,11R,15RS)-9-bromo-11,15-dihydroxy-15-methyl-5,13-prostadienoic acid, a compound of claim 1.

24. (13E)-(9R,11R,15S,16RS)-9-bromo-11,15-dihydroxy-16,19-dimethyl-13,18-prostadienoic acid, a compound of claim 1.

25. (13E)-(9S,11R,15S,16RS)-9-bromo-11,15-dihydroxy-16,19-dimethyl-13,18-prostadienoic acid, a compound of claim 1.

26. (5Z,13E)-(9R,11R,15R)-9-bromo-11,15-dihydroxy-16,16,19-trimethyl-5,13,18-prostatrienoic acid, a compound of claim 1.

27. (5Z,13E)-(9S,11R,15R)-9-bromo-11,15-dihydroxy-16,16,19-trimethyl-5,13,18-prostatrienoic acid, a compound of claim 1.

28. (13E)-(9R,11R,15R)-9-bromo-1,11,15-trihydroxy-16-phenoxy-17,18,19,20-tetranor-13-prostene, a compound of claim 1.

29. (13E)-(9S,11R,15R)-9-bromo-1,11,15-trihydroxy-16-phenoxy-17,18,19,20-tetranor-13-prostene, a compound of claim 1.

30. (13E)-(9R,11R,15R)-9-bromo-11,15-dihydroxy-16-phenoxy-17,18,19,20-tetranor-13-prostenoic acid methylsulfonamide, a compound of claim 1.

31. (13E)-(9S,11R,15R)-9-bromo-11,15-dihydroxy-16-phenoxy-17,18,19,20-tetranor-13-prostenoic acid methylsulfonamide, a compound of claim 1.

32. (13E)-(9R,11R,15R)-9-bromo-11,15-dihydroxy-16-phenoxy-17,18,19,20-tetranor-13-prostenoic acid amide, a compound of claim 1.

33. (13E)-(9R,11R,15R)-9-bromo-11,15-dihydroxy-16-phenoxy-17,18,19,20-tetranorprostenoic acid tris(hydroxymethyl)aminomethane salt, a compound of claim 1.

34. A pharmaceutical composition comprising an amount of a compound of claim 1 effective as a cytoprotective agent and a pharmaceutically acceptable carrier.

35. A method of inducing a cytoprotective effect in a patient in need of such treatment comprising administering to the patient an amount of a compound of claim 1 effective as a cytoprotective agent.

36. A composition of claim 2 wherein $R_1$ is $COOR_2$ and $R_2$ is (a) to (e).

37. A composition of claim 2 wherein $R_1$ is $COOR_3$ and $R_2$ is (a) to (e).

* * * * *